United States Patent
Libbus et al.

(10) Patent No.: US 8,983,598 B2
(45) Date of Patent: Mar. 17, 2015

(54) SYSTEM FOR NEURALLY-MEDIATED ANTI-ARRHYTHMIC THERAPY

(75) Inventors: Imad Libbus, St. Paul, MN (US); Joseph M. Pastore, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1135 days.

(21) Appl. No.: 11/538,488

(22) Filed: Oct. 4, 2006

(65) Prior Publication Data

US 2008/0086174 A1  Apr. 10, 2008

(51) Int. Cl.
- *A61N 1/00* (2006.01)
- *A61N 1/36* (2006.01)
- *A61N 1/39* (2006.01)
- *A61N 1/05* (2006.01)

(52) U.S. Cl.
CPC .......... *A61N 1/36114* (2013.01); *A61N 1/3956* (2013.01); *A61N 1/0504* (2013.01)
USPC ................................................... 607/5; 607/7

(58) Field of Classification Search
USPC ........................................................ 607/5, 7
See application file for complete search history.

(56) References Cited

U.S. PATENT DOCUMENTS

| | | |
|---|---|---|
| 4,727,877 A | 3/1988 | Kallok |
| 4,953,551 A * | 9/1990 | Mehra et al. ................. 607/5 |
| 5,107,834 A | 4/1992 | Ideker et al. |
| 5,203,326 A | 4/1993 | Collins |
| 5,203,348 A | 4/1993 | Dahl et al. |
| 5,342,407 A | 8/1994 | Dahl et al. |
| 5,360,442 A | 11/1994 | Dahl et al. |
| 5,405,363 A | 4/1995 | Kroll et al. |
| 5,431,683 A | 7/1995 | Bowald et al. |
| 5,464,429 A | 11/1995 | Hedberg et al. |
| 5,468,254 A | 11/1995 | Hahn et al. |
| 5,496,362 A | 3/1996 | KenKnight et al. |
| 5,522,853 A | 6/1996 | Kroll |
| 5,540,723 A | 7/1996 | Ideker et al. |
| 5,545,202 A | 8/1996 | Dahl et al. |
| 5,603,732 A | 2/1997 | Dahl et al. |

(Continued)

FOREIGN PATENT DOCUMENTS

| | | |
|---|---|---|
| EP | 0688577 A1 | 12/1995 |
| EP | 0688578 A1 | 12/1995 |

(Continued)

OTHER PUBLICATIONS

PCT Application No. PCT/US2007/069010, Invitation to Pay Additional Fees and Partial International Search Report mailed Jan. 17, 2008, 7 pgs.

(Continued)

*Primary Examiner* — Catherine Voorhees
(74) *Attorney, Agent, or Firm* — Schwegman Lundberg & Woessner, P.A.

(57) ABSTRACT

According to an embodiment of a method, a predetermined cardiac activity indicated for an antitachycardia shock is detected. Neural stimulation is applied to lower a defibrillation threshold in preparation for the shock, and the shock is subcutaneously delivered. According to one embodiment, neural stimulation is applied as part of a prophylactic therapy. A predetermined cardiac activity indicated for an antitachycardia shock is detected, and the shock is subcutaneously delivered. Other aspects and embodiments are provided herein.

31 Claims, 7 Drawing Sheets

(56) References Cited

U.S. PATENT DOCUMENTS

| | | |
|---|---|---|
| 5,662,689 A | 9/1997 | Elsberry et al. |
| 5,697,953 A | 12/1997 | Kroll et al. |
| 5,718,718 A | 2/1998 | Kroll et al. |
| 5,792,187 A | 8/1998 | Adams |
| 5,797,967 A | 8/1998 | KenKnight |
| 5,817,131 A | 10/1998 | Elsberry et al. |
| 5,827,326 A | 10/1998 | Kroll et al. |
| 5,836,976 A | 11/1998 | Min et al. |
| 5,893,881 A | 4/1999 | Elsberry et al. |
| 5,916,243 A | 6/1999 | KenKnight et al. |
| 5,954,752 A | 9/1999 | Mongeon et al. |
| 5,957,956 A | 9/1999 | Kroll et al. |
| 5,978,705 A | 11/1999 | KenKnight et al. |
| 6,002,962 A | 12/1999 | Huang et al. |
| 6,026,332 A | 2/2000 | Kenknight et al. |
| 6,032,079 A | 2/2000 | KenKnight et al. |
| 6,038,483 A | 3/2000 | KenKnight et al. |
| 6,134,470 A | 10/2000 | Hartlaub |
| 6,152,955 A | 11/2000 | KenKnight et al. |
| 6,275,730 B1 | 8/2001 | KenKnight et al. |
| 6,400,982 B2 | 6/2002 | Sweeney et al. |
| 6,408,213 B1 | 6/2002 | Bartig et al. |
| 6,571,125 B2 | 5/2003 | Thompson |
| 6,574,514 B2 | 6/2003 | Partridge et al. |
| 6,647,292 B1 | 11/2003 | Bardy et al. |
| 6,721,597 B1 | 4/2004 | Bardy et al. |
| 6,842,648 B2 | 1/2005 | Partridge et al. |
| 6,931,278 B1 * | 8/2005 | Kroll et al. ............ 607/5 |
| 6,952,610 B2 | 10/2005 | Ostroff et al. |
| 6,988,003 B2 | 1/2006 | Bardy et al. |
| 6,999,814 B2 | 2/2006 | Hauser et al. |
| 7,039,459 B2 | 5/2006 | Bardy et al. |
| 7,043,299 B2 | 5/2006 | Erlinger et al. |
| 7,069,080 B2 | 6/2006 | Bardy et al. |
| 7,076,294 B2 | 7/2006 | Bardy et al. |
| 7,225,017 B1 | 5/2007 | Shelchuk |
| 7,321,793 B2 * | 1/2008 | Ezra et al. ............ 607/5 |
| 7,657,311 B2 | 2/2010 | Bardy et al. |
| 7,720,534 B2 | 5/2010 | Bardy et al. |
| 8,090,438 B2 | 1/2012 | Bardy et al. |
| 8,255,049 B2 | 8/2012 | Li |
| 2002/0042630 A1 | 4/2002 | Bardy et al. |
| 2002/0068958 A1 | 6/2002 | Bardy et al. |
| 2002/0082658 A1 | 6/2002 | Heinrich et al. |
| 2002/0103510 A1 | 8/2002 | Bardy et al. |
| 2002/0111601 A1 | 8/2002 | Thompson |
| 2002/0147407 A1 | 10/2002 | Seim |
| 2003/0074027 A1 | 4/2003 | Chen et al. |
| 2003/0078623 A1 | 4/2003 | Weinberg et al. |
| 2003/0181951 A1 | 9/2003 | Cates |
| 2003/0191403 A1 | 10/2003 | Zhou et al. |
| 2003/0212436 A1 * | 11/2003 | Brown ............ 607/5 |
| 2003/0236558 A1 | 12/2003 | Whitehurst et al. |
| 2004/0098059 A1 | 5/2004 | Chen et al. |
| 2004/0172071 A1 | 9/2004 | Bardy et al. |
| 2004/0193231 A1 | 9/2004 | David et al. |
| 2004/0220629 A1 | 11/2004 | Kamath et al. |
| 2004/0225332 A1 | 11/2004 | Gebhardt et al. |
| 2004/0254612 A1 * | 12/2004 | Ezra et al. ............ 607/5 |
| 2005/0065553 A1 | 3/2005 | Ezra et al. |
| 2005/0131464 A1 | 6/2005 | Heinrich et al. |
| 2005/0143776 A1 | 6/2005 | Brown |
| 2005/0187584 A1 * | 8/2005 | Denker et al. ............ 607/5 |
| 2005/0187585 A1 | 8/2005 | Mussig et al. |
| 2006/0015164 A1 | 1/2006 | Pridge et al. |
| 2006/0116729 A1 | 6/2006 | Chen et al. |
| 2006/0136001 A1 | 6/2006 | Ortega et al. |
| 2006/0206154 A1 * | 9/2006 | Moffitt et al. ............ 607/9 |
| 2006/0253157 A1 | 11/2006 | Libbus et al. |
| 2006/0259084 A1 * | 11/2006 | Zhang et al. ............ 607/9 |
| 2006/0293714 A1 | 12/2006 | Salo et al. |
| 2007/0100380 A1 | 5/2007 | Fukui |
| 2007/0260283 A1 | 11/2007 | Li |
| 2008/0015659 A1 | 1/2008 | Zhang et al. |
| 2008/0065158 A1 | 3/2008 | Ben-Ezra et al. |
| 2008/0086175 A1 | 4/2008 | Libbus et al. |
| 2009/0198294 A1 | 8/2009 | Rossing et al. |
| 2012/0296383 A1 | 11/2012 | Li et al. |

FOREIGN PATENT DOCUMENTS

| | | |
|---|---|---|
| EP | 1304135 A2 | 4/2003 |
| JP | 08-038626 A | 2/1996 |
| JP | 2004-508149 A | 3/2004 |
| JP | 2004-351122 A | 12/2004 |
| JP | 2009-536558 A | 10/2009 |
| WO | WO-00/27474 A1 | 5/2000 |
| WO | WO-0027474 A1 | 5/2000 |
| WO | WO-02/22208 A2 | 3/2002 |
| WO | WO-2004/105870 A1 | 12/2004 |
| WO | WO-2006/039694 A2 | 4/2006 |
| WO | WO-2006/098996 A1 | 9/2006 |
| WO | WO-2006/121836 A1 | 11/2006 |
| WO | WO-2007/133877 A2 | 11/2007 |
| WO | WO-2008/042468 A2 | 4/2008 |
| WO | WO-2008042468 A3 | 4/2008 |

OTHER PUBLICATIONS

Ando, M., et al., "Efferent Vagal Nerve Stimulation Protects Heart Against Ischemia-Induced Arrhythmias by Preserving Connexin43 Protein", *Circulation*, 112(2), (2005), 164-170.

Chen, Victor T., et al., "Methods and Apparatus for Termination of Cardiac Tachyarrhythmias", U.S. Appl. No. 09/448,648, filed Nov. 24, 1999, 19 pgs.

Kenknight, B. H., "Marked Reduction of Ventricular Defibrillation Threshold by Application of an Auxiliary Shock to a Catheter Electrode in the Left Posterior Coronary Vein of Dogs", *J Cardiovasc Electrophysiol.*, 11(8), (2000), 900-906.

Kouakam, C., et al., "Effect of elevated heart rate preceding the onset of ventricular tachycardia on antitachycardia pacing effectiveness in patients with implantable cardioverter defibrillators.", *American Journal of Cardiology*, 92(1), (2003), 26-32.

Murakawa, Y., et al., "Effect of Cervical Vagal Nerve Stimulation on Defibrillation Energy: a Possible Adjunct to Efficient Defibrillation", *Japanese Heart Journal*, 44(1), (2003), 91-100.

Shelchuk, A. M., "Optimisation of ICD therapy-DFT how to reduce it ?", *EUROPACE*, vol. 7 No. S1 (2005), 105-106.

Takahashi, N., "Vagal modulation of ventricular tachyarrhythmias induced by left ansae subclaviae stimulation in rabbits", *Japanese Heart Journal*, 39(4), (1998), 503-511.

Ternes, David, et al., "Neural Stimulation Systems, Devices and Methods", U.S. Appl. No. 11/610,234, filed Dec. 13, 2006, 46 pgs.

Vanoli, E., et al., "Vagal Stimulation and Prevention of Sudden Death in Conscious Dogs with a Healed Myocardial Infarction", *Circulation Research*, 68(5) (1991), 1471-1481.

Zamotrinsky, A. V., et al., "Vagal Neurostimulation in Patients with Coronary Artery Disease.",*Auton Neurosci.*, 88(1-2), (Apr. 12, 2001),109-16.

"PCT Application No. PCT/US2007/069010, International Search Report mailed Apr. 22, 2008", 7 pgs.

"PCT Application No. PCT/US2007/069010, Written Opinion mailed Apr. 22, 2008", 10 pgs.

"U.S. Appl. No. 11/760,987, Non-Final Office Action mailed Feb. 24, 2009", 9 pgs.

"U.S. Appl. No. 11/382,120, Response to Restriction Requirement, mailed Sep. 30, 2009", 10 pgs.

"U.S. Appl. No. 11/382,120, Resriction Requirement mailed Sep. 4, 2009", 5 pgs.

"U.S. Appl. No. 11/760,987, Response filed May 26, 2009 to Non Final Office Actio mailed Feb. 24, 2009", 13 pgs.

"U.S. Appl. No. 11/760,987, Response to Restriction Requirement, mailed Oct. 8, 2009", 8 pgs.

"U.S. Appl. No. 11/760,987, Restriction Requirement mailed Sep. 9, 2009", 7 Pgs.

"U.S. Appl. No. 12/422,147, Preliminary Statement filed Apr. 10, 2009", 2 pgs.

"U.S. Appl. No. 11/760,987 Non-Final Office Action mailed Nov. 24, 2009", 10 pgs.

(56) References Cited

OTHER PUBLICATIONS

"U.S. Appl. No. 11/760,987, Final Office Action mailed May 12, 2010", 9 pgs.
"U.S. Appl. No. 11/760,987, Response filed Feb. 24, 2010 to Non Final Office Action mailed Nov. 24, 2010", 11 pgs.
"U.S. Appl. No. 11/382,120, Non-Final Office Action mailed Nov. 27, 2009.", 11 pgs.
"U.S. Appl. No. 11/382,120, Final Office Action mailed Jul. 8, 2010", 12 pgs.
"U.S. Appl. No. 11/382,120, Response filed Mar. 29, 2010 to Non Final Office Action mailed Nov. 27, 2009", 13 pgs.
"U.S. Appl. No. 11/760,987, Response filed Jul. 27, 2010 to Final Office Action mailed May 12, 2010", 11 pgs.
"European Application Serial No. 07783811.8, Communication mailed Jun. 17, 2010", 4 pgs.
"Japanese Patent Application Serial No. 2009-531494, Amended Claims filed Mar. 31, 2010", (w/ English Translation), 11 pgs.
"U.S. Appl. No. 11/382,120, Response filed Sep. 8, 2010 to Final Office Action mailed Jul. 8, 2010", 14 pgs.
"U.S. Appl. No. 11/382,120, Non Final Office Action mailed Mar. 30, 2011", 14 pgs.
"U.S. Appl. No. 11/760,987, Non Final Office Action mailed Dec. 27, 2010", 9 pgs.
"European Serial No. 07783811.8 Office Action Response filed Dec. 16, 2010 to Office Action mailed Jun. 17, 2010", 11 pgs.
"U.S. Appl. No. 11/382,120, Notice of Allowance mailed Apr. 3, 2012", 10 pgs.
"U.S. Appl. No. 11/382,120, PTO Response to Rule 312 Communication mailed Aug. 1, 2010", 2 pgs.
"Japanese Application Serial No. 2009-509919, Office Action mailed Jan. 20, 2010", (w/ English Translation of Amended Claims), 11 pgs.
"Japanese Application Serial No. 2009-509919, Office Action mailed Jan. 20, 2012", (w/ English Translation of Amened Claims), 5 pgs.
"Japanese Application Serial No. 2009-509919, Response Filed Apr. 10, 2012 to Office Action mailed Jan. 20, 2012", (w/ English Translation of Amened Claims), 11 pgs.
"Japanese Application No. 2009-531494, Office Action mailed Jul. 9, 2012", (w/ English Translation), 5 pgs.
"U.S. Appl. No. 11/382,120 Response to Non Final Office Action mailed Mar. 30, 2011", 13 pgs.
"U.S. Appl. No. 11/382,120, Final Office Action mailed Oct. 28, 2011", 8 pgs.
"U.S. Appl. No. 11/760,987, Final Office Action mailed Jul. 1, 2011", 9 pgs.
"U.S. Appl. No. 11/760,987, Response filed Apr. 27, 2011 to Non Final Office Action mailed Dec. 27, 2010", 12 pgs.
"U.S. Appl. No. 11/382,120, Advisory Action mailed Jan. 31, 2012", 3 pgs.
"U.S. Appl. No. 11/382,120, Advisory Action mailed Oct. 1, 2010", 6 pgs.
"U.S. Appl. No. 11/382,120, Examiner Interview Summary mailed Aug. 11, 2011", 4 pgs.
"U.S. Appl. No. 11/382,120, Response filed Dec. 28, 2011 to Final Office Action mailed Oct. 28, 2011", 11 pgs.
"U.S. Appl. No. 11/760,987, Examiner Interview Summary mailed May 5, 2011", 3 pgs.
"Japanese Application Serial No. 2009-531494, Office Action mailed Jan. 17, 2012", (w/ English Translation), 7 pgs.
"U.S. Appl. No. 13/569,208, Advisory Action mailed Feb. 25, 2014", 6 pages.
"U.S. Appl. No. 13/569,208, Examiner Interview Summary mailed Feb. 25, 2014", 3 pages.
"U.S. Appl. No. 13/569,208, Final Office Action mailed Oct. 25, 2013", 12 pages.
"U.S. Appl. No. 13/569,208, Non Final Office Action mailed Apr. 2, 2013", 10 pages.
"U.S. Appl. No. 13/569,208, Non Final Office Action mailed Apr. 2, 2014", 12 pages.
"U.S. Appl. No. 13/569,208, Response filed Jan. 21, 2014, to Final Office Action mailed Oct. 25, 2013", 11 pages.
"U.S. Appl. No. 13/569,208, Response filed Feb. 26, 2014, to Final Office Action mailed Nov. 25, 2013", 12 pages.
"U.S. Appl. No. 13/569,208, Response filed Mar. 18, 2013, to Restriction Requirement mailed Feb. 15, 2013", 10 pages.
"U.S. Appl. No. 13/569,208, Response filed Jul. 1, 2014, to Non Final Office Action mailed Apr. 2, 2014", 11 pages.
"U.S. Appl. No. 13/569,208, Response filed Jul. 2, 2013, to Non Final office Action mailed Apr. 2, 2013", 10 pages.
"U.S. Appl. No. 13/569,208, Restriction Requirement mailed Feb. 15, 2013", 7 pages.
"European Application Serial No. 07783811.8, Office Action mailed Oct. 4, 2012", 5 pages.
"European Application Serial No. 07783811.8, Response filed Dec. 21, 2012, to Examination Notification Art. 94(3) mailed Oct. 4, 2012", 13 pages.
"European application Serial No. 12169618.1, Extended European Search Report mailed Jan. 24, 2013", 6 pages.
"European Application Serial No. 12169618.1, Office Action mailed Feb. 21, 2013", 6 pages.
"European Application Serial No. 12169618.1, Partial Search Report mailed Oct. 9, 2012", 9 pages.
"European Application Serial No. 12169618.1, Response filed Jun. 17, 2013 to Examination Notification Art. 94(3) mailed Feb. 21, 2013", 10 pages.
"Japanese Application Serial No. 2009-531,494, Examiners Decision of Final Refusal mailed Feb. 12, 2013", 5 pages.
"Japanese Application Serial No. 2009-531494, Response filed Nov. 29, 2012, Office Action mailed Jul. 9, 2012", With English Claims, 27 pages.
Zamotrinsky, A V, et al., "Vagal neurostimulation in patients with coronary artery disease", Autonomic Neuroscience-Base & Clinical, 88(1-2). (Apr. 12, 2001), 109-116.

* cited by examiner

SYSTEM FOR NEURALLY-MEDIATED ANTI-ARRHYTHMIC THERAPY

FIELD

This application relates generally to medical devices and, more particularly, to systems, devices and methods for providing neurally-mediated anti-arrhythmic therapy.

BACKGROUND

The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. Contractions of the myocardium provide these pumping functions. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony, which efficiently pumps the blood. Blocked or abnormal electrical conduction or deteriorated myocardial tissue causes dysynchronous contraction of the heart, resulting in poor hemodynamic performance, including a diminished blood supply to the heart and the rest of the body. Heart failure occurs when the heart fails to pump enough blood to meet the body's metabolic needs.

Tachyarrhythmias are abnormal heart rhythms characterized by a rapid heart rate. Examples of tachyarrhythmias include supraventricular tachycardias (SVTs) such as atrial tachycardia (AT), and atrial fibrillation (AF), and the more dangerous ventricular tachyarrhythmias which include ventricular tachycardia (VT) and ventricular fibrillation (VF). Abnormal ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Many abnormal ventricular rhythms exhibit an abnormal QRS complex in an electrocardiogram because the depolarization spreads from the excitatory focus or point of re-entry directly into the myocardium rather than through the normal ventricular conduction system. Ventricular tachycardia is typically characterized by distorted QRS complexes that occur at a rapid rate, while ventricular fibrillation is diagnosed when the ventricle depolarizes in a chaotic fashion with no identifiable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion, an electrical shock delivered to the heart synchronously with the QRS complex, and defibrillation, an electrical shock delivered without synchronization to the QRS complex, can be used to terminate most tachyarrhythmias. Cardioversion and defibrillation are referred generally herein as antitachycardia shocks. The electric shock terminates the tachyarrhythmia by simultaneously depolarizing the myocardium and rendering it refractory. A class of cardiac rhythm management (CRM) devices known as an implantable cardioverter defibrillator (ICD) provides this kind of therapy by delivering a shock pulse to the heart when the device detects tachyarrhythmias. One type of ICD is a subcutaneous ICD. However, the defibrillation threshold (DFT) for a subcutaneous ICD is significantly elevated as compared to an intracardiac ICD.

SUMMARY

According to an embodiment of a method, a predetermined cardiac activity indicated for an antitachycardia shock is detected. Neural stimulation is applied to lower a defibrillation threshold in preparation for the shock, and the shock is subcutaneously delivered. According to one embodiment, neural stimulation is applied as part of a prophylactic therapy. A predetermined cardiac activity indicated for an antitachycardia shock is detected, and the shock is subcutaneously delivered.

An embodiment of a system includes a sensor, a vagal nerve stimulator, and a defibrillator. The sensor is adapted to detect a predetermined cardiac activity indicated for a defibrillation shock. The vagal nerve stimulator is adapted to deliver vagal nerve stimulation. The defibrillator is adapted to subcutaneously deliver the defibrillation shock. Various embodiments include a vagal nerve stimulator adapted to deliver neural stimulation to lower a defibrillation threshold for the defibrillation shock. Various embodiments include a vagal nerve stimulator adapted to deliver neural stimulation as part of a prophylactic therapy.

An embodiment of an implantable device comprises a shock pulse generator, a cardiac activity sensor, a nerve stimulator and a microprocessor. The shock pulse generator is adapted to subcutaneously deliver an antitachycardia shock using at least one subcutaneous lead with at least one electrode. The cardiac activity sensor is adapted to detect cardiac activity signals. The nerve stimulator generator is adapted to deliver vagal nerve stimulation. The microprocessor is adapted to detect a predetermined cardiac activity indicated for the antitachycardia shock using the cardiac activity detected by the cardiac activity sensor, to control the nerve stimulator generator to deliver vagal nerve stimulation, and to control the shock pulse generator to deliver the antitachycardia shock. According to various embodiments, the microprocessor is adapted to control the nerve stimulator generator to deliver nerve stimulation to lower a defibrillation threshold in response to detecting the predetermined cardiac activity, and to control the shock pulse generator to deliver the antitachycardia shock after delivering the vagal nerve stimulation. According to various embodiments, the microprocessor is adapted to control the nerve stimulator generator to prophylactically deliver nerve stimulation.

An embodiment of a system comprises a neural stimulator adapted to deliver vagal nerve stimulation to lower a defibrillation threshold, and a subcutaneous implantable cardioverter defibrillator (ICD) adapted to deliver an antitachycardia shock. The neural stimulator and the subcutaneous ICD are adapted to communicate allowing the neural stimulator to lower the defibrillation threshold after an antitachycardia event has occurred in preparation for delivery of the antitachycardia shock.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

An embodiment includes an implantable device adapted to provide subcutaneous anti-arrhythmic therapy, and to provide vagal stimulation to suppress and prevent tachyarrhythmias such as ventricular tachycardia (VT) or ventricular fibrillation (VF). The vagal stimulation can be delivered intermittently or in response to sensed cardiac activity. An embodiment of the device is adapted to respond to the detection of a potentially lethal tachyarrhythmia by delivering a subcutaneous antitachycardia shock, using synchronous vagal stimulation to lower the defibrillation threshold (DFT) and enhance the efficacy of the shock therapy. In various embodiments, the vagal stimulation significantly decreases the DFT. The illustrated embodiment of the device includes an implantable pulse generator connected to a neural stimulation lead for vagal nerve stimulation. Vagal nerve stimulation is applied intermittently, or in response to sensed cardiac activity predetermined to be an indicator of potentially lethal tachyarrhythmias. An example of such cardiac activity includes ST-segment elevation detected by wireless ECG. The subcutaneous device includes cardiac sensing and defibrillation capabilities, and is adapted to detect tachyarrhythmias (such as VT/VF) and deliver an antitachycardia shock. In various embodiments, the device is adapted to deliver vagal nerve stimulation for a short period of time (e.g. 5-7 seconds) before applying the shock to lower the DFT and counteract the inefficient shock delivery. Without the application of vagal nerve stimulation, the DFT for a subcutaneous ICD is significantly elevated as compared to an intracardiac ICD.

Various embodiments provide two implantable units that communicate wirelessly. One unit is placed in the pectoral region, and connected to a neural stimulation lead for vagal nerve stimulation. The other unit is placed abdominally, and is responsible for cardiac sensing and cardioversion/defibrillation. In yet another embodiment, both units are involved in the cardiac sensing and/or cardioversion/defibrillation.

In an embodiment, vagal nerve stimulation is applied intermittently, such as ten seconds per minute, to prevent or abate progression of cardiac disease development. Abating disease progression includes preventing the disease progression, or slowing down or reducing the intensity of the disease progression. In this case, the portion of the device responsible for cardiac sensing and cardioversion/defibrillation monitors heart rate, and ensures that the heart rate does not fall below unacceptable levels during vagal nerve stimulation. Other parameters such as blood pressure or minute ventilation can be used to assess the appropriateness of the neural stimulation. If heart rate falls below a programmable threshold, the device adjusts the stimulation (e.g. reducing the amount or turning off the vagal nerve stimulation).

A subcutaneous ICD with vagal stimulation capability can be used by any patient at elevated risk for cardiac arrhythmias, and is believed to be particularly beneficial for patients with moderately-elevated risk who likely would not receive an ICD with intracardiac leads.

Figure 1:
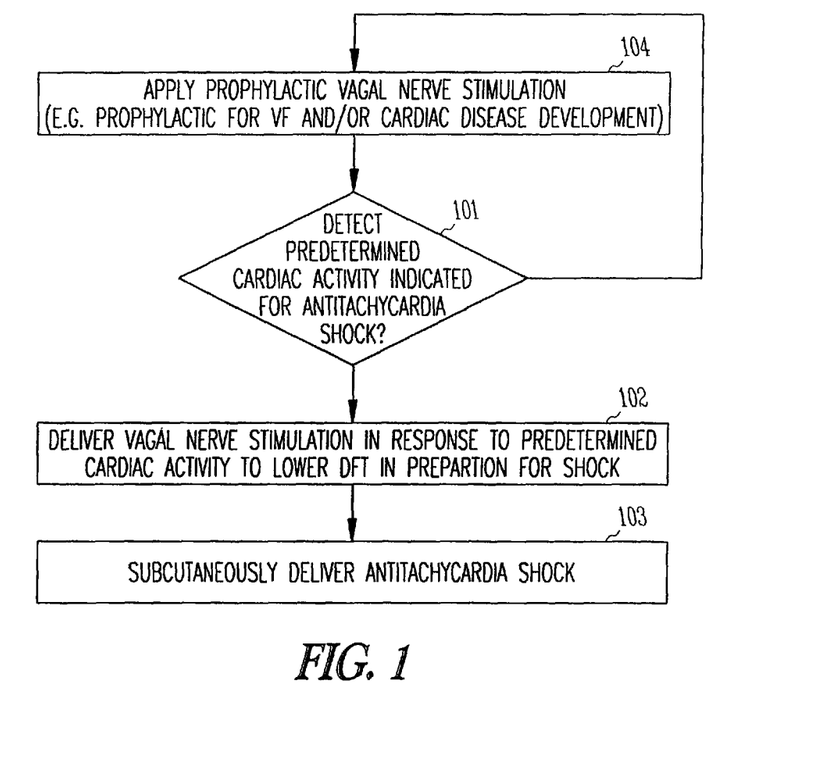
FIG. 1 illustrates a method according to various embodiments.

FIG. 1 illustrates a method according to various embodiments. The illustrated method includes, at 101, detecting a predetermined cardiac activity that has been indicated for an antitachycardia shock. Various embodiments use the lead(s) of a subcutaneous ICD to detect the predetermined cardiac activity. Various embodiments use electrodes on a housing of a subcutaneously implanted device to detect the predetermined cardiac activity. Various embodiments detect the predetermined cardiac activity using a wireless EEG, which uses only electrodes on the subcutaneously implanted device to detect the cardiac activity. An example of cardiac activity that has been indicated for an antitachycardia shock includes an elevated ST-segment. When it is determined that a shock should be applied, the process proceeds to 102 to deliver vagal nerve stimulation in response to predetermined cardiac activity to lower a defibrillation threshold (DFT) in preparation for the antitachycardia shock. The vagal nerve stimulation can be delivered through a lead to a vagus nerve in the cervical region. Various embodiments use a lead with a nerve cuff electrode. Various embodiments use a transvascular lead fed into the internal jugular vein, or other vessel, to place at least one electrode proximate to a vagus nerve. Various embodiments use satellite electrodes in wireless communication with the subcutaneous defibrillator. The satellite electrodes can be self powered or can receive power wirelessly (e.g. through ultrasound transducers that recharge batteries or deliver power as needed for the stimulation). The shock is subcutaneously delivered, as illustrated at 103.

Various embodiments apply prophylactic vagal nerve stimulation, as illustrated at 104. The prophylactic vagal nerve stimulation can be provided as a therapy in addition to the nerve stimulation therapy to lower DFT, or can be provided as a therapy without the nerve stimulation therapy to lower DFT. Modulation of the sympathetic and parasympathetic nervous system with neural stimulation has been shown to have positive clinical benefits, such as protecting the myocardium from further remodeling and predisposition to fatal arrhythmias following a myocardial infarction. One example of a prophylactic vagal nerve stimulation includes stimulation delivered to prevent ventricular fibrillation, such as may be applied after a myocardial infarction. Although the mechanisms are not completely understood at present, various studies have indicated that sympathetic hyperactivity often triggers life-threatening ventricular arrhythmias in the setting of acute myocardial ischemia. Another example of a prophylactic vagal nerve stimulation includes stimulation to prevent development of a cardiac disease, such as anti-remodeling therapy.

Figure 2:
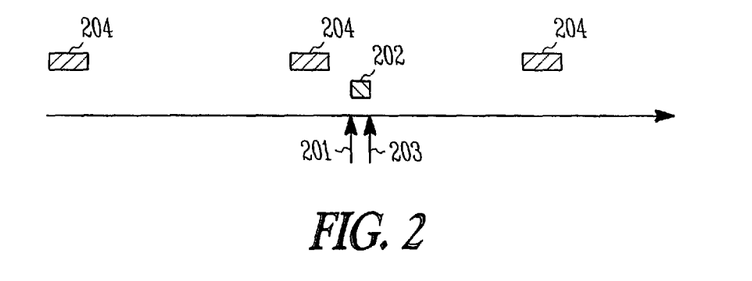
FIG. 2 illustrates a timing diagram for an example of the method illustrated in FIG. 1.

FIG. 2 illustrates a timing diagram for an example of the method illustrated in FIG. 1. As illustrated at 204, vagal nerve stimulation is delivered intermittently as part of a prophylactic therapy. For example, the prophylactic therapy can be delivered on a schedule, such as 5 minutes every hour. Arrow 201 illustrates a time when it is determined that it is appropriate or desirable to provide an antitachycardia shock. As illustrated at 202 vagal nerve stimulation is delivered to lower a defibrillation threshold (DFT) in anticipation of the shock. Various embodiments deliver the neural stimulation to lower the DFT for less than one minute, various embodiments deliver the neural stimulation to lower the DFT for less than 15 seconds, and various embodiments deliver the neural stimulation for a duration between approximately 5 seconds to approximately 7 seconds. At 203, a subcutaneous defibrillator delivers a defibrillation shock after the DFT has been lowered. According to various embodiments, for example, the shock is delivered within one minute after initiating the neural stimulation to lower the DFT. Various embodiments deliver the shock within 20 seconds after initiating the neural stimulation to lower the DFT. Various embodiments deliver the shock within 10 seconds after initiating the neural stimulation to lower the DFT. The DFT will not be lowered if the neural stimulation is delivered for too long of a duration before the defibrillation shock is delivered. Various embodiments terminate the neural stimulation delivered to lower DFT at or approximately when the shock is delivered.

Figure 3:
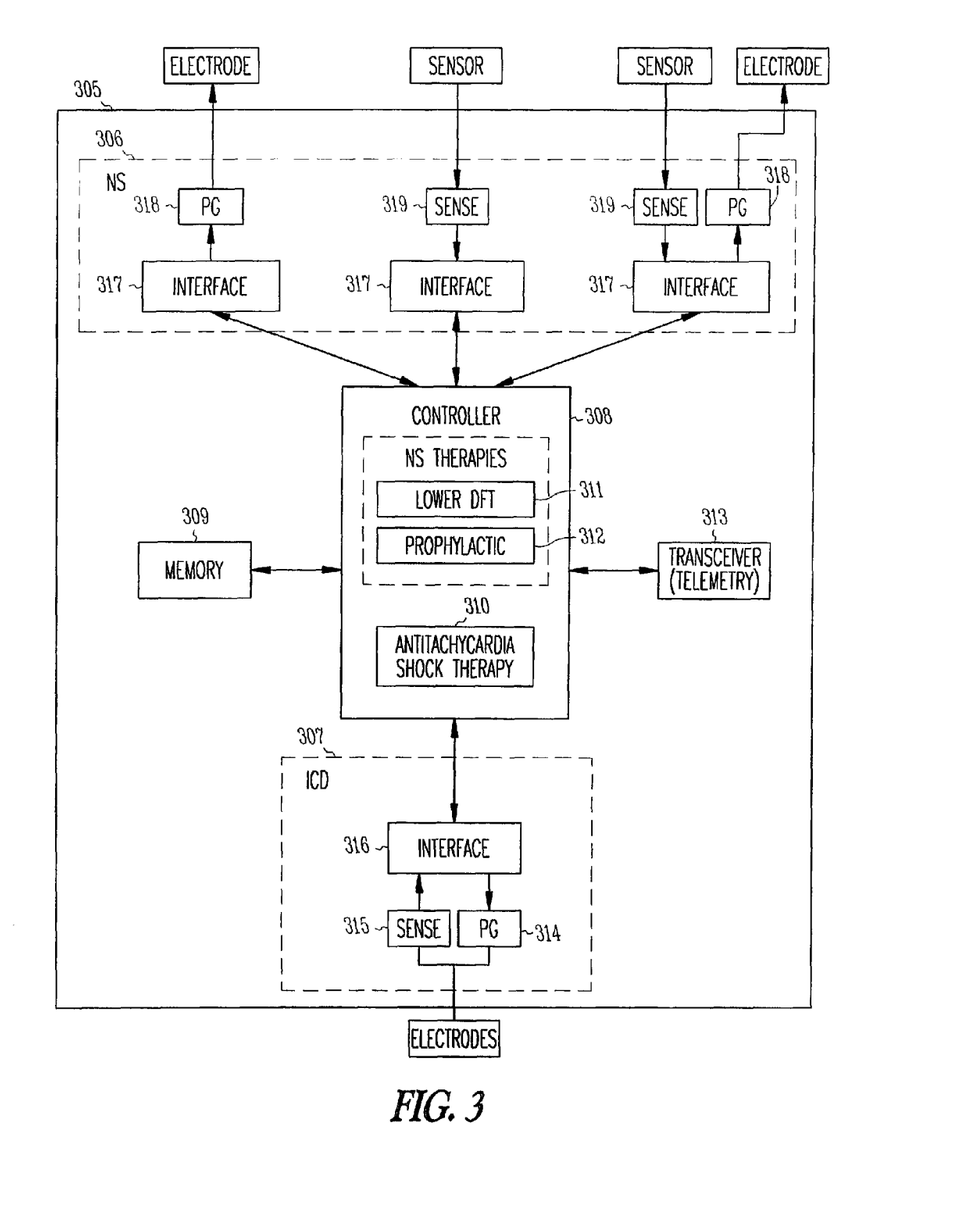
FIG. 3 illustrates an embodiment of implantable medical device (IND) having a neural stimulation (NS) component and an implantable cardioverter defibrillator (ICD) component.

FIG. 3 illustrates an IMD 305 having a neural stimulation (NS) component 306 and ICD component 307, according to various embodiments of the present subject matter. The illustrated device includes a controller 308 and memory 309. According to various embodiments, the controller includes hardware, software, or a combination of hardware and software to perform the neural stimulation and ICD functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and ICD functions. An example of an ICD function includes antitachycardia shock therapy 310 such as may include cardioversion or defibrillation, and examples of NS functions include parasympathetic stimulation and/or sympathetic inhibition to lower DFT 311, and parasympathetic stimulation and/or sympathetic inhibition as part of a prophylactic therapy 312 such as a therapy to prevent or diminish cardiac remodeling and/or a therapy applied after a myocardial infarction to prevent ventricular fibrillation. The controller also executes instructions to detect a tachyarrhythmia. The illustrated device further includes a transceiver 313 and associated circuitry for use to communicate with a programmer or another external or internal device. Various embodiments include a telemetry coil.

The ICD therapy section 307 includes components, under the control of the controller, to stimulate a heart and/or sense cardiac signals using one or more electrodes. The illustrated ICD therapy section includes a pulse generator 314 for use to provide an electrical signal through electrodes to stimulate a heart, and further includes sense circuitry 315 to detect and process sensed cardiac signals. An interface 316 is generally illustrated for use to communicate between the controller 308 and the pulse generator 314 and sense circuitry 315. The present subject matter is not limited to a particular number of electrode sites.

The NS therapy section 306 includes components, under the control of the controller, to stimulate a neural stimulation target, and in some embodiments sense parameters associated with nerve activity or surrogates of nerve activity such as blood pressure and respiration. Three interfaces 317 are illustrated in the NS therapy section 306. However, the present subject matter is not limited to a particular number interfaces, or to any particular stimulating or sensing functions. Pulse generators 318 are used to provide electrical pulses to electrode(s) or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. The controller can control the initiation and termination of neural stimulation pulse trains. Sense circuits 319 are used to detect and process signals from a sensor, such as a sensor of nerve activity, blood pressure, respiration, and the like. The interfaces 317 are generally illustrated for use to communicate between the controller 308 and the pulse generator 318 and sense circuitry 319. Each interface, for example, may be used to control a separate lead. Various embodiments of the NS therapy section only include a pulse generator to stimulate or inhibit a neural target such as a vagus nerve.

Figure 4:
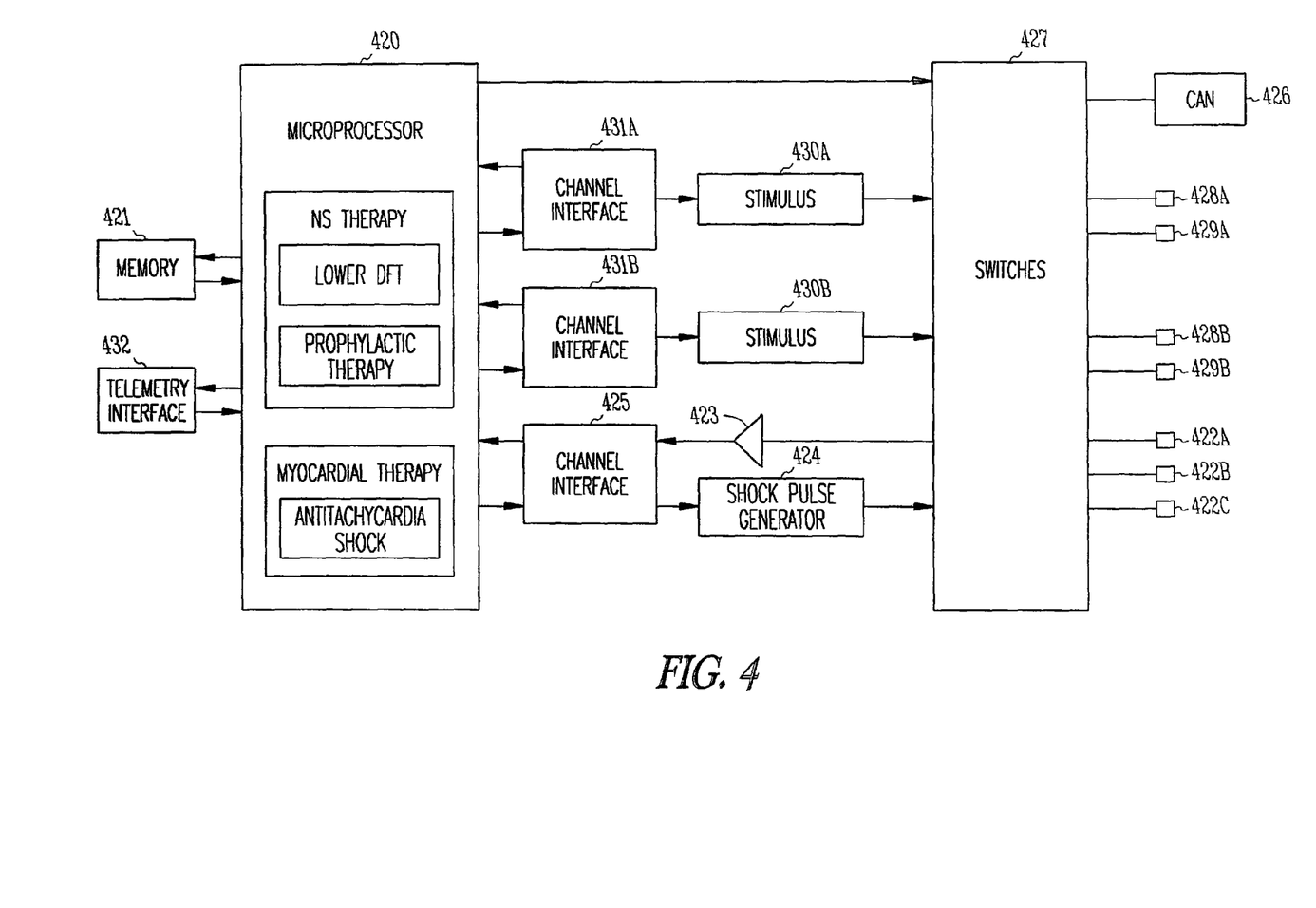
FIG. 4 illustrates an embodiment of a microprocessor-based implantable device.

FIG. 4 shows a system diagram of an embodiment of a microprocessor-based implantable device, according to various embodiments. The controller of the device is a microprocessor 420 which communicates with a memory 421 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

The illustrated device includes an ICD channel that includes electrodes 422A, 422B and 422C, a sensing amplifier 423 for use in detecting cardiac activity using at least some of electrodes 422A, 422B and 422C, a shock pulse generator 424 for use in delivering an antitachycardia shock using at least some of electrodes 422A, 422B and 422C, and a channel interface 425 adapted to communicate bidirectionally with microprocessor 420. Although three electrodes are illustrated, the ICD channel can use more or fewer electrodes, including at least one can electrode 426. Wireless EEG, for example, can be detected using can electrodes. The interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry detects a chamber sense, either an atrial sense or ventricular sense, when an electrogram signal (i.e., a voltage sensed by an electrode representing cardiac electrical activity) generated by a particular channel exceeds a specified detection threshold. Such senses can be used to detect a cardiac rhythm that is indicated for a defibrillation shock. The intrinsic atrial and/or ventricular rates can be measured by measuring the time intervals between atrial and ventricular senses, respectively, and used to detect atrial and ventricular tachyarrhythmias.

The illustrated electrodes are connected via conductors within the lead to a switching network 427 controlled by the microprocessor. The switching network is used to switch the electrodes to the input of a sense amplifier in order to detect intrinsic cardiac activity and to the output of a pulse generator in order to deliver an antitachycardia shock. The switching network also enables the device to sense or shock either in a bipolar mode using lead electrodes or in a unipolar mode using a lead electrode and the device housing (can) 426 or an electrode on another lead serving as a ground electrode.

Neural stimulation channels, identified as channels A and B, are incorporated into the device for delivering parasympathetic stimulation and/or sympathetic inhibition, where one channel includes a bipolar lead with a first electrode 428A and a second electrode 429A, a pulse generator 430A, and a channel interface 431A, and the other channel includes a bipolar lead with a first electrode 428B and a second electrode 429B, a pulse generator 430B, and a channel interface 431B. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be subcutaneously tunneled or intravascularly disposed near an appropriate stimulation site. Other types of leads and/or electrodes may also be employed. A nerve cuff electrode may be used around the cervical vagus nerve bundle to provide parasympathetic stimulation or around the aortic or carotid sinus nerve to provide sympathetic inhibition. In an embodiment, the leads of the neural stimulation electrodes are replaced by wireless links, and the electrodes for providing parasympathetic stimulation and/or sympathetic inhibition are incorporated into satellite units.

The figure illustrates a telemetry interface 432 connected to the microprocessor, which can be used to communicate with an external device. The illustrated microprocessor 420 is capable of performing neural stimulation therapy routines and myocardial stimulation routines. Examples of NS therapy routines include an NS therapy to lower DFT, and an NS prophylactic therapy to prevent ventricular fibrillation after a myocardial infarction, or to prevent progression of cardiac disease. Examples of myocardial therapy routines include an antitachycardia shock therapy such as cardioversion/defibrillation.

Figure 5:
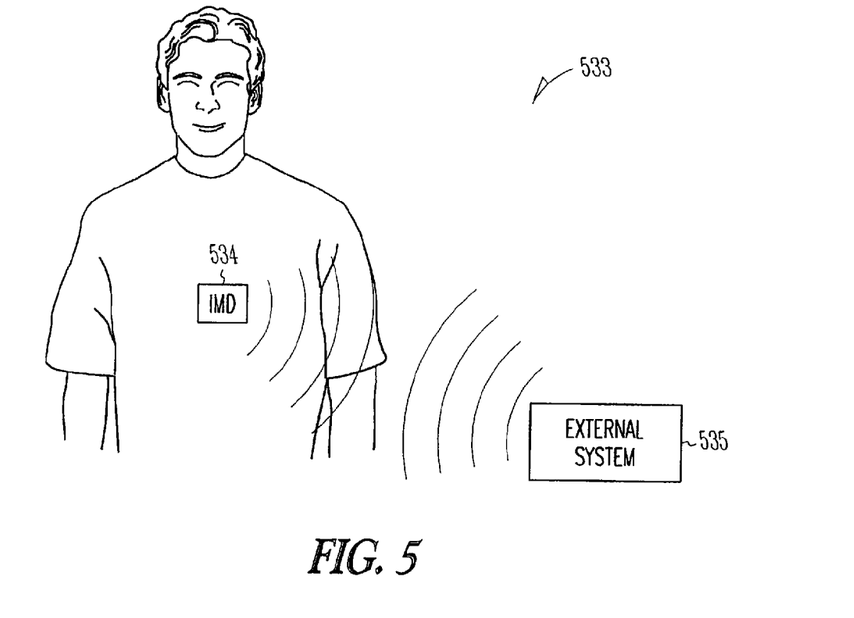
FIG. 5 illustrates a system embodiment including an implantable medical device (IMD) and an external system or device.

FIG. 5 illustrates a system 533 including an IMD 534 and an external system or device 535, according to various embodiments of the present subject matter. Various embodiments of the IMD 534 include a combination of NS and ICD functions. The external system 535 and the IMD 534 are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates a neural target to lower DFT in preparation for a shock, and subcutaneously delivers the shock. Various embodiments of the IMD also deliver a programmed neural stimulation therapy as part of a prophylactic treatment for ventricular fibrillation or ventricular remodeling.

The external system allows a user such as a physician or other caregiver or a patient to control the operation of IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by the IMD, extracting physiological data acquired by and stored in IMD, extracting therapy history data stored in implantable medical device, and extracting data indicating an operational status of the IMD (e.g., battery status and lead impedance). Telemetry link also provides for data transmission from external system to the IMD. This includes, for example, programming the IMD to acquire physiological data, programming the IMD to perform at least one self-diagnostic test (such as for a device operational status), and programming the IMD to deliver at least one therapy.

Figure 6:
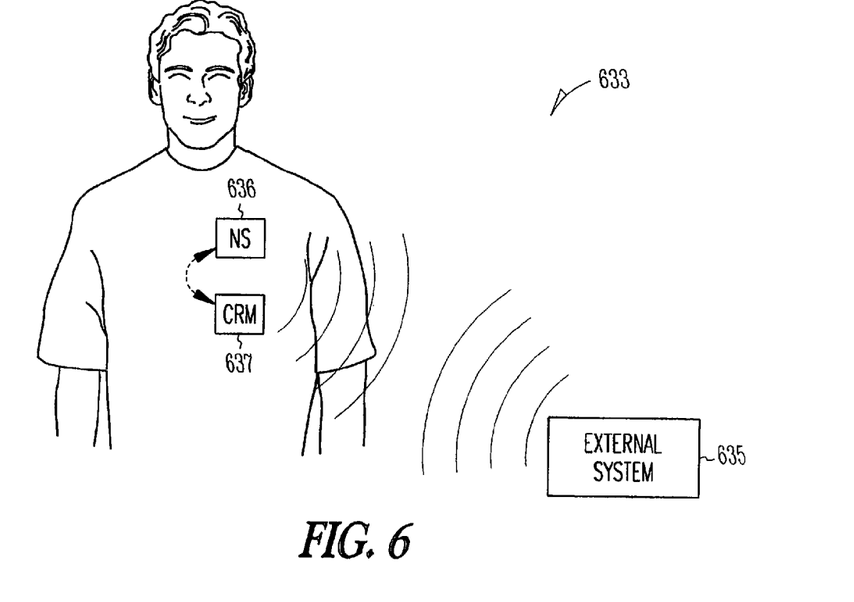
FIG. 6 illustrates a system embodiment including an external device, an implantable neural stimulator (NS) device and an ICD device.

FIG. 6 illustrates a system 633 including an external device 635, an implantable neural stimulator (NS) device 636 and a subcutaneous ICD 637, according to various embodiments of the present subject matter. Various aspects involve a method for communicating between an NS device and the ICD. The illustrated NS device and the ICD are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and ICD devices, various embodiments provide a communication cable or wire, such as an intravenously-fed lead, for use to communicate between the NS device and the ICD device. In some embodiments, the external system functions as a communication bridge between the NS and ICD devices.

Figure 7:
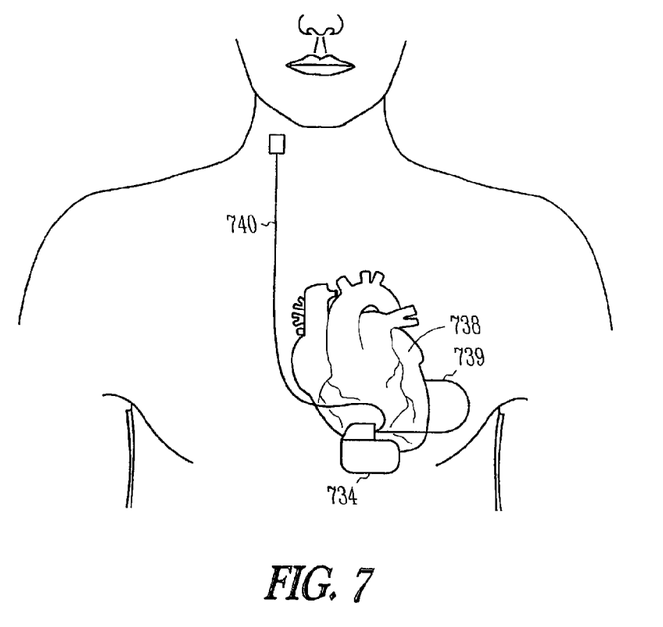
FIG. 7 illustrates an embodiment of a subcutaneous ICD with vagal nerve stimulation.

FIG. 7 illustrates an embodiment of a subcutaneous ICD with vagal nerve stimulation. The location of the device 734 is in a subcutaneous space that is developed during the implantation process, and the heart 738 is not exposed during this process. The subcutaneous space is below the patient's skin and over muscle tissue and the rib cage. The lead 739 of the subcutaneous electrode traverses in a subcutaneous path around the thorax terminating with its distal electrode lateral to the left scapula to deliver current between the can and electrode to the majority of the ventricular myocardium. A distal electrode on the lead is a coil electrode that is used for delivering the cardioversion/defibrillation energy across the heart. The lead can also include sense electrodes spaced a distance to provide good QRS detection. The sensing of QRS waves can be carried out using sense electrodes on the housing of the device 734 or using a combination of lead electrodes and housing electrodes. The sensing vectors between electrodes can be adjusted to provide the best detection of cardiac activity. When a shock is to be applied, the sensing electrodes can be turned off and isolated from damage caused by the shock. A neural stimulation lead 740 extends from the device 734 to a vagal target. The neural stimulation lead 740 can be tunneled subcutaneously to the vagus nerve, or can be transvascularly fed to the internal jugular vein adjacent to the vagus nerve. Satellite electrodes may be used to deliver neural stimulation.

Figure 8:
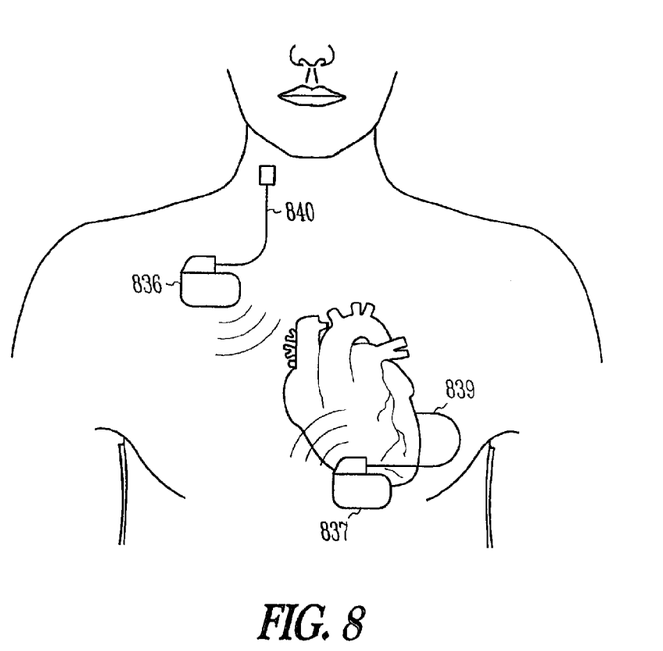
FIG. 8 illustrates an embodiment of a system, including a subcutaneous ICD and an implantable vagal nerve stimulator.

FIG. 8 illustrates an embodiment of a system, including a subcutaneous ICD 837 and an implantable vagal nerve stimulator 836. The ICD 837 has a subcutaneous lead 839 similar to the lead 739 described with respect to FIG. 7. A separate vagal nerve stimulator 836 includes a neural stimulation lead 840, which can be tunneled subcutaneously to the vagus nerve, or can be transvascularly fed to the internal jugular vein adjacent to the vagus nerve. The ICD and nerve stimulator are adapted to communicate with each other. The illustrated system illustrates wireless communication between the devices, such as may be achieved using ultrasound or radiofrequency signals. A subcutaneously tunneled tether can connect the two implanted devices, and communication and/or power can be provided through the tether. Thus, the neural stimulation to lower the DFT can be coordinated with the delivery of the subcutaneous defibrillation.

Figure 9:
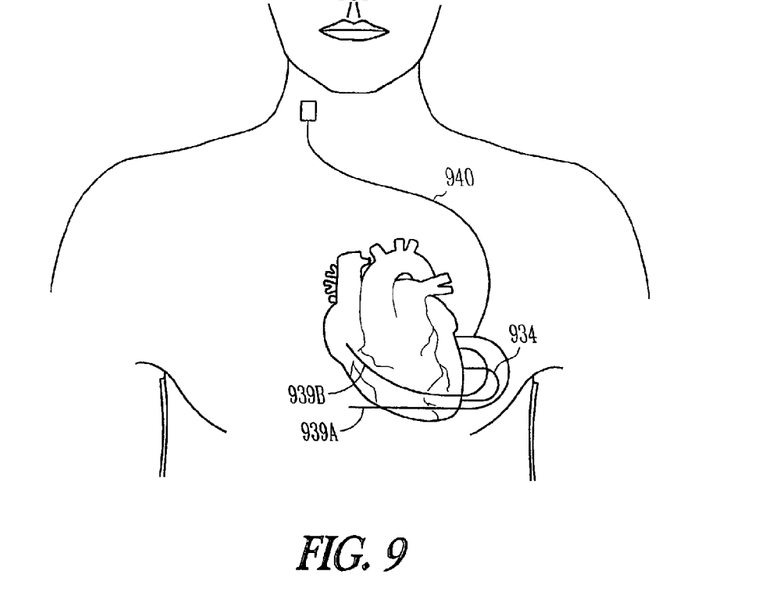
FIG. 9 illustrates an embodiment of a subcutaneous ICD with vagal nerve stimulation.

FIG. 9 illustrates an embodiment of a subcutaneous ICD with vagal nerve stimulation. In the illustrated embodiment, there are two subcutaneous leads 939A and 939B connected to the ICD 934. The cardioversion/defibrillation energy can be delivered between the active surface of the device housing and electrodes on each lead. The desired electrodes for sensing and/or shocking can be selected by the device. A neural stimulation lead 940 extends from the device 934 to a vagal target. The neural stimulation lead 940 can be tunneled subcutaneously to the vagus nerve, or can be transvascularly fed to the internal jugular vein adjacent to the vagus nerve. Satellite electrodes may be used to deliver neural stimulation.

Figure 10:
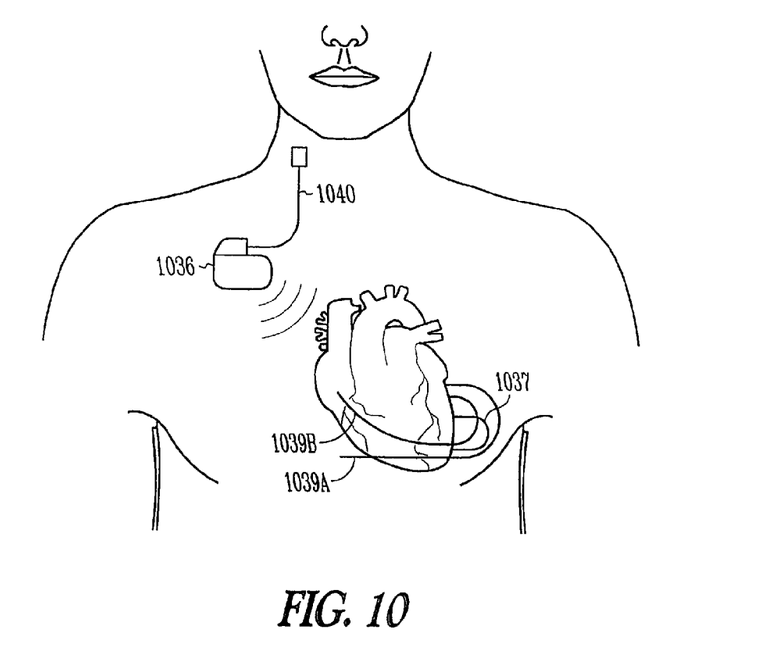
FIG. 10 illustrates an embodiment of a system, including a subcutaneous ICD and an implantable vagal nerve stimulator.

FIG. 10 illustrates an embodiment of a system, including a subcutaneous ICD 1037 and an implantable vagal nerve stimulator 1036. The ICD 1037 has subcutaneous leads 1039A and 1039B similar to the leads 939A and 939B described with respect to FIG. 9. A separate vagal nerve stimulator 1036 includes a neural stimulation lead 1040, which can be tunneled subcutaneously to the vagus nerve, or can be transvascularly fed to the internal jugular vein adjacent to the vagus nerve. The ICD and nerve stimulator are adapted to communicate with each other. The illustrated system illustrates wireless communication between the devices, such as may be achieved using ultrasound or radiofrequency signals. A subcutaneously tunneled tether can connect the two implanted devices, and communication and/or power can be provided through the tether. Thus, the neural stimulation to lower the DFT can be coordinated with the delivery of the subcutaneous defibrillation.

Figure 11:
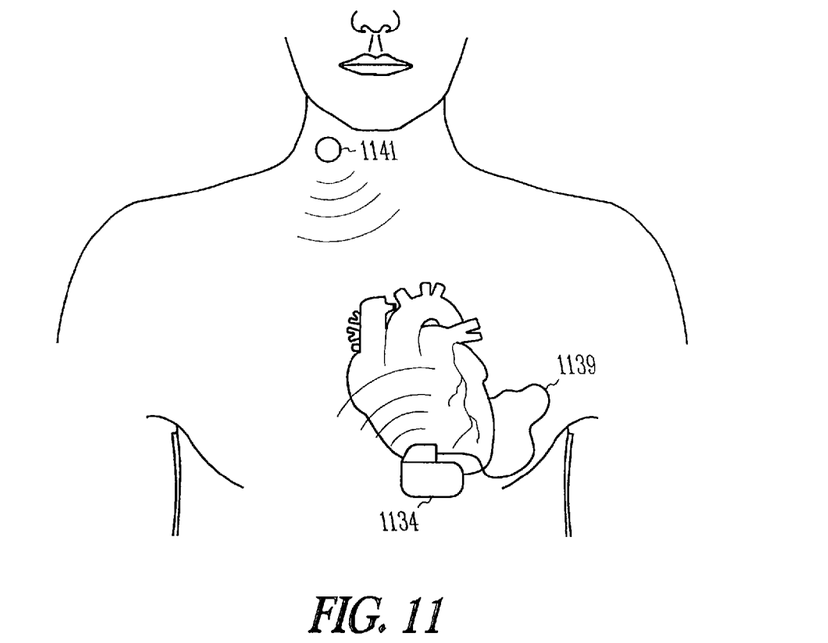
FIG. 11 illustrates an embodiment of a subcutaneous ICD with vagal nerve stimulation.

FIG. 11 illustrates an embodiment of a subcutaneous ICD with vagal nerve stimulation. The illustrated ICD 1134 provides vagal nerve stimulation using satellite electrodes 1141. The satellite electrode can include its own power, and can wirelessly communicate with the ICD. The satellite electrodes can include nerve cuff electrodes, transvascular electrodes, and subcutaneous electrodes. The subcutaneous ICD 1134 may be used in adults where chronic transvenous/epicardial ICD lead systems pose excessive risk or have already resulted in difficulty such as sepsis or lead fractures, and may be used for use in children whose growth poses problems with transvenous ICDs. FIG. 11 also illustrates the placement of the subcutaneous lead 1139, which is fed in a serpentine fashion rather than a taught configuration. As the child grows, the bends in the lead straighten allowing the proper electrode placement to be maintained. An anchor can be used to fix the distal end of the lead.

Figure 12:
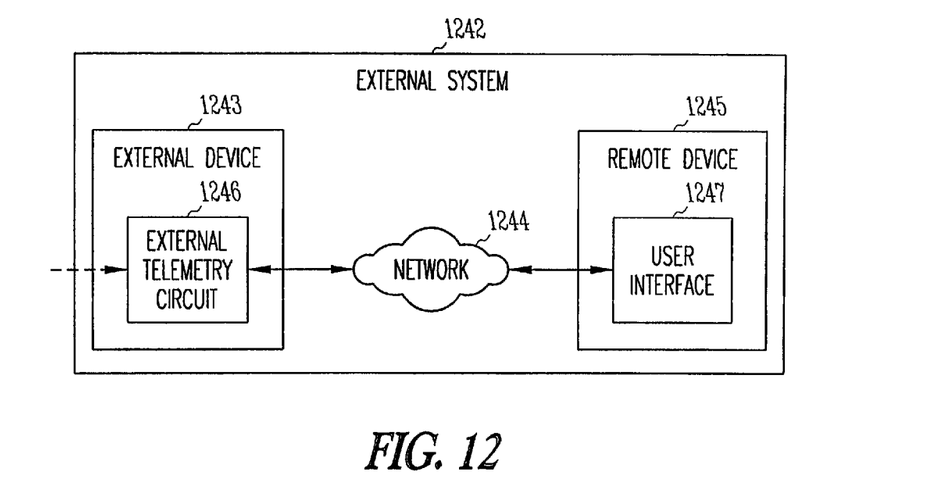
FIG. 12 is a block diagram illustrating an embodiment of an external system.

FIG. 12 is a block diagram illustrating an embodiment of an external system 1242. The external system includes a programmer, in some embodiments. In the embodiment illustrated in FIG. 12, the external system includes a patient management system. As illustrated, external system 1242 is a patient management system including an external device 1243, a telecommunication network 1244, and a remote device 1245. The external device 1243 is placed within the vicinity of an IMD and includes external telemetry system 1246 to communicate with the IMD. Remote device(s) 1245 is in one or more remote locations and communicates with the external device 1243 through the network 1244, thus allowing a physician or other caregiver to monitor and treat a patient from a distant location and/or allowing access to various treatment resources from the one or more remote locations. The illustrated remote device 1245 includes a user interface 1247.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium. One of ordinary skill in the art will understand that the modules and other circuitry shown and described herein can be implemented using software, hardware, and combinations of software and hardware.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A method, comprising:
   detecting a predetermined cardiac activity indicated for an antitachycardia shock;
   applying neural stimulation with a subcutaneous electrode to lower a defibrillation threshold in preparation for the shock; and
   subcutaneously delivering the shock from a subcutaneous non-intrathoracic space, wherein subcutaneously delivering the shock includes delivering energy between at least two electrodes operatively positioned in the subcutaneous space to deliver energy across the heart.

2. The method of claim 1, further comprising applying neural stimulation as part of a prophylactic therapy.

3. The method of claim 2, wherein the prophylactic therapy includes intermittent vagal stimulation to prevent ventricular fibrillation.

4. The method of claim 2, wherein the prophylactic therapy includes intermittent vagal stimulation to prevent development of a cardiac disease.

5. The method of claim 2, wherein applying neural stimulation as part of the prophylactic therapy includes monitoring heart rate, and adjusting the neural stimulation if the heart rate falls below a programmable threshold.

6. The method of claim 1, wherein applying neural stimulation to lower a defibrillation threshold includes initiating the neural stimulation to lower the defibrillation threshold less than 10 seconds before delivering the shock.

7. The method of claim 1, wherein applying neural stimulation to lower a defibrillation threshold includes applying neural stimulation for a duration between approximately 5 to approximately 7 seconds.

8. The method of claim 1, wherein subcutaneously delivering the shock includes delivering the shock between at least one electrode on at least one subcutaneously implanted lead and an electrode on a subcutaneously implanted device housing.

9. The method of claim 1, wherein applying the neural stimulation includes applying vagal stimulation with the subcutaneous electrode.

10. The method of claim 1, wherein:
    subcutaneously delivering the shock includes using an implantable device to subcutaneously deliver the shock; and
    applying the neural stimulation includes applying the neural stimulation using a satellite electrode configured to wirelessly communicate with the implantable device.

11. A system, comprising:
    a sensor adapted to detect a predetermined cardiac activity indicated for a defibrillation shock;
    a vagal nerve stimulator adapted to use a subcutaneous electrode to deliver vagal nerve stimulation; and
    a defibrillator including at least two electrodes configured to be operatively positioned in a subcutaneous non-intrathoracic space to deliver energy across the heart, wherein the defibrillator is configured to subcutaneously deliver the defibrillation shock between the at least two electrodes operatively positioned in the subcutaneous non-intrathoracic space to deliver energy across the heart,
    wherein the vagal nerve stimulator is adapted to:
       deliver vagal nerve stimulation to lower a defibrillation threshold for the defibrillation shock; or
       deliver intermittent vagal nerve stimulation as a prophylactic therapy to prevent ventricular fibrillation after a myocardial infarction; or
       deliver intermittent vagal nerve stimulation as a prophylactic therapy to prevent or abate progression of cardiac disease.

12. The system of claim 11, wherein the sensor is adapted to detect the predetermined cardiac activity using at least one electrode, and the defibrillator is adapted to subcutaneously deliver the defibrillation shock using the at least one electrode used to detect the predetermined cardiac activity.

13. The system of claim 11, including one implantable device housing adapted to house both the vagal nerve stimulator and the defibrillator.

14. The system of claim 11, including a first implantable housing adapted to house the vagal nerve stimulator and a second implantable housing adapted to house the defibrillator.

15. The system of claim 14, wherein the first implantable housing includes the sensor adapted to detect the predetermined cardiac activity.

16. The system of claim 14, wherein the second implantable housing includes the sensor adapted to detect the predetermined cardiac activity.

17. The system of claim 11, wherein the vagal nerve stimulator is adapted to deliver vagal nerve stimulation to lower a defibrillation threshold for the defibrillation shock.

18. The system of claim 11, wherein a self-powered, implantable satellite device includes the subcutaneous electrode to deliver vagal stimulation.

19. An implantable device, comprising:
    at least one subcutaneous lead with at least one electrode configured to be operatively placed in a subcutaneous non-intrathoracic space;
    a shock pulse generator configured to subcutaneously deliver an antitachycardia shock between at least two electrodes operatively positioned in the subcutaneous non-intrathoracic space to deliver energy across the heart, wherein the shock pulse generator is configured to use the at least one subcutaneous lead with the at least one electrode to deliver energy across the heart;
    a cardiac activity sensor adapted to detect cardiac activity signals;
    a nerve stimulator generator adapted to use a subcutaneous electrode to deliver vagal nerve stimulation; and
    a microprocessor adapted to detect a predetermined cardiac activity indicated for the antitachycardia shock using the cardiac activity detected by the cardiac activity sensor, to control the shock pulse generator to deliver the antitachycardia shock, and to control the nerve stimulator generator to:
    deliver vagal nerve stimulation to lower DFT in preparation for the antitachycardia shock, or
    deliver vagal nerve stimulation to prevent ventricular fibrillation after a myocardial infarction, or
    deliver vagal nerve stimulation to prevent or abate progression of cardiac disease.

20. The device of claim 19, the subcutaneous electrode includes a satellite electrode.

21. The device of claim 19, wherein the microprocessor is adapted to control the nerve stimulator generator to deliver nerve stimulation to lower a defibrillation threshold in response to detecting the predetermined cardiac activity, and to control the shock pulse generator to deliver the antitachycardia shock after delivering the vagal nerve stimulation.

22. The device of claim 21, wherein the microprocessor is adapted to control the nerve stimulator generator to deliver vagal nerve stimulation to lower a defibrillation threshold for a duration between approximately 5 seconds to approximately 7 seconds.

23. The device of claim 21, wherein the microprocessor is adapted to control the shock pulse generator to deliver the antitachycardia shock within one minute after initiating the vagal nerve stimulation to lower the defibrillation threshold.

24. The device of claim 21, wherein the microprocessor is adapted to control the shock pulse generator to deliver the antitachycardia shock within 10 seconds after initiating the vagal nerve stimulation to lower the defibrillation threshold.

25. The device of claim 19, wherein the microprocessor is adapted to control the nerve stimulator generator to deliver nerve stimulation as part of a prophylactic therapy.

26. The system of claim 19, wherein a self-powered, implantable satellite device includes the subcutaneous electrode to deliver vagal stimulation.

27. A system, comprising:
a neural stimulator adapted to use a subcutaneous electrode to deliver vagal nerve stimulation to lower a defibrillation threshold; and
a subcutaneous non-intrathoracic implantable cardioverter defibrillator (ICD) including at least two electrodes configured to be operatively positioned in a subcutaneous non-intrathoracic space to deliver energy across the heart, wherein the subcutaneous non-intrathoracic ICD is configured to deliver an antitachycardia shock between the at least two electrodes and across the heart, wherein the neural stimulator and the subcutaneous non-intrathoracic ICD are adapted to communicate allowing the neural stimulator to lower the defibrillation threshold after an antitachycardia event has occurred in preparation for delivery of the antitachycardia shock.

28. The system of claim 27, wherein the subcutaneous non-intrathoracic ICD is adapted to detect a predetermined cardiac activity indicated for the antitachycardia shock.

29. The system of claim 27, wherein the neural stimulator is adapted to deliver vagal nerve stimulation to lower the defibrillation threshold for a duration less than 10 seconds before subcutaneous non-intrathoracic ICD delivers the antitachycardia shock.

30. The system of claim 27, wherein a self-powered, implantable satellite device includes the subcutaneous electrode to deliver vagal stimulation.

31. The system of claim 30, wherein the satellite device is configured to wirelessly communicate with the subcutaneous non-intrathoracic ICD.

* * * * *